United States Patent [19]

Poittevin et al.

[11] 4,073,919
[45] Feb. 14, 1978

[54] HYPOLIPEMIANT COMPOSITIONS AND METHODS

[75] Inventors: André Poittevin, Vaires-sur-Marne; Vesperto Torelli, Maisons-Alfort, both of France

[73] Assignee: Roussel Uclaf, Paris, France

[21] Appl. No.: 654,629

[22] Filed: Feb. 2, 1976

[30] Foreign Application Priority Data

Feb. 14, 1975 France ............................. 75 04627
Dec. 12, 1975 France ............................. 75 38062

[51] Int. Cl.$^2$ ......................................... A61K 31/425
[52] U.S. Cl. .................. 424/270; 260/302 R; 560/177
[58] Field of Search ............... 260/302 R; 424/270

[56] References Cited

U.S. PATENT DOCUMENTS 3,681,088  8/1972  Katz et al. .................. 260/302 R 3,957,809  5/1976  Hardy et al. ..................... 424/270

Primary Examiner—R. Gallagher
Attorney, Agent, or Firm—Hammond & Littell

[57] ABSTRACT

Novel 5-thiazole alkanols of the formula

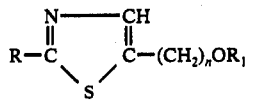

I wherein R is alkyl of 1 to 5 carbon atoms, $n$ is an integer from 2 to 7 and $R_1$ is selected from the group consisting of hydrogen and acyl of an alkanoic acid of 2 to 6 carbon atoms and their non-toxic, pharmaceutically acceptable acid addition salts having a marked antilipolytic activity and useful as intermediates and their preparation.

6 Claims, No Drawings 4,073,919

HYPOLIPEMIANT COMPOSITIONS AND METHODS

STATE OF THE ART

Zubarovskii et al. [Chem. Ab., Vol. 58 (1963), p. 2525b] describes the preparation of 2-methyl-thiazole-5-methanol by reacting lithium aluminum hydride with ethyl 2-methyl-thiazole-5-carboxylate but does not describe any pharmacological properties therefore.

Copending, commonly assigned U.S. patent application Ser. No. 495,556 filed Aug. 8, 1974, now U.S. Pat. No. 3,957,809, describes thiazole derivatives of the formula $$R-C\underset{S}{\overset{N-CH}{\diagdown\diagup}}C-CH_2OR_1 \qquad A$$

wherein R is alkyl of 2 to 12 carbon atoms and $R_1$ is selected from the group consisting of hydrogen, alkyl of 1 to 8 carbon atoms and acyl of an organic carboxylic acid of 1 to 12 carbon atoms having hypolipemiant activity and a prolonged vasodilatatory activity.

OBJECTS OF THE INVENTION

It is an object of the invention to provide the novel products of formula I and their non-toxic, pharmaceutically acceptable acid addition salts.

It is a further object of the invention to provide novel hypolipemiant compositions and to provide a novel method of inducing hypolipemic activity in warm-blooded animals.

These and other objects and advantages of the invention will become obvious from the following detailed description.

THE INVENTION

The novel 5-thiazole alkanols of the invention are selected from the group consisting of compounds of the formula $$R-C\underset{S}{\overset{N-CH}{\diagdown\diagup}}C-(CH_2)_nOR_1 \qquad I$$

wherein R is alkyl of 1 to 5 carbon atoms, $n$ is an integer from 2 to 7 and $R_1$ is selected from the group consisting of hydrogen and acyl of an alkanoic acid of 2 to 6 carbon atoms and their non-toxic, pharmaceutically acceptable acid addition salts.

Examples of R are methyl, ethyl, propyl, butyl, isobutyl, isopropyl, tert.-butyl or pentyl. Examples of $-(CH_2)_n-$ are methylene, ethylene, propylene, butylene and pentylene. Examples of suitable alkanoic acids for the acyl of $R_1$ are acetic acid, propionic acid, butyric acid, isobutyric acid and valeric acid.

Examples of suitable acids for the preparation of the non-toxic, pharmaceutically acceptable acid addition salts are strong mineral acids such as hydrochloric acid, hydrobromic acid, hydroiodic acid, nitric acid, sulfuric acid or phosphoric acid and strong organic acids such as alkyl monosulfonic acids such as methane sulfonic acid, ethane sulfonic acid and propane sulfonic acid, alkyl disulfonic acids such as methane disulfonic acid, α,β-disulfonic acid and aryl monosulfonic acids and aryl disulfonic acids such as benzene sulfonic acid.

Among the preferred compounds of formula I are those where $n$ is an integer from 2 to 6 and $R_1$ is hydrogen. More preferably, $n$ is an odd number of $R_1$ is hydrogen. Specific preferred compounds of formula I are 2-methyl-5-thiazolepropanol and 2-propyl-5-thiazolepentanol.

The novel process for the preparation of the 5-thiazole alkanols of formula I wherein $R_1$ is hydrogen comprises reacting a compound of the formula $$R-C\underset{S}{\overset{N-CH}{\diagdown\diagup}}C-(CH_2)_n'-COOR_1' \qquad II$$

wherein R has the above definition, $n'$ is an integer from 1 to 6 and $R_1'$ is hydrogen or alkyl of 1 to 5 carbon atoms with a reducing agent to obtain a compound of formula I wherein $R_1$ is hydrogen which may then be reacted with a lower alkanoic acid of 2 to 6 carbon atoms or a functional derivative thereof to obtain the corresponding compound of formula I wherein $R_1$ is an acyl group.

Preferably, the reducing agent is a mixed hydride such as lithium aluminum hydride or lithium borohydride and the reduction is effected in an organic solvent such as dioxane, tetrahydrofuran or ethyl ether. Most preferably, the reaction is effected with lithium aluminum hydride in tetrahydrofuran.

The acylation may be effected with the free acid or a functional derivative such as the acid anhydride or the acid halide such as the acid bromide or chloride. The acylation is preferably effected in the presence of a mineral base such as sodium hydroxide or potassium hydroxide or an organic base such as pyridine, collidine or triethylamine. The non-toxic, pharmaceutically acceptable acid addition salts may be prepared by reacting the compound of formula I with a strong mineral or organic acid.

The compounds of formula II may be prepared as described in our copending, commonly assigned application Ser. No. 659,514 filed on even date herewith entilted Novel Thiazole Alkanoic Acids wherein alkylthioamide of the formula $$R-\overset{S}{\overset{\|}{C}}-NH_2 \qquad B$$

wherein R has the above definition is reacted with a compound of the formula $$HC-\underset{Hal}{\overset{O}{\overset{\|}{C}}H}-(CH_2)_{n'}-COOR_2 \qquad C$$

wherein $n'$ has the above definition, Hal is chlorine or bromine and $R_2$ is alkyl of 1 to 5 carbon atoms to obtain the compound of formula II wherein $R_1'$ is alkyl of 1 to 5 carbon atoms which may be hydrolyzed to the corresponding free acid of formula II.

The alkylthioamides of formula B may be prepared by the process of Gilbert et al. [Chem. Ab., Vol. 65, 20020e] and the compounds of formula C may be prepared by reacting an ester of the formula

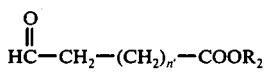

wherein $R_2$ and $n'$ have the above definition in an organic solvent with bromine as described in Helv. Chim. Acta, Vol. 33 (1950), p. 503 or with chlorine gas. The esters of formula D are known or may be made by hydrolyzing known esters followed by esterification.

The compounds of formula I are useful as intermediates for the preparation of thiazole alkane carbamates of the formula

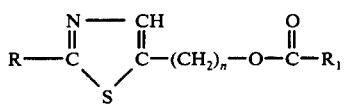

wherein R and $n$ have the above definition and $R_1$ is $NH_2-$, phenylamino, diphenylamino, loweralkylamino and diloweralkylamino which also possess antilipolytic acitivity as described in our copending, commonly assigned application Ser. No. 654,630 filed on even date herewith entitled Novel Thiazole Derivatives. The compounds of formula I and their non-toxic, pharmaceutically acceptable acid addition salts also possess marked antilipolytic activity which diminishes the level of the plasmatic free fatty acids.

The novel hypolipemiant composition of the invention are comprised of an effective amount of at least one compound of formula I and their non-toxic, pharmaceutically acceptable acid addition salts and a pharmaceutical carrier.

Particularly active are the compounds of formula I wherein $n$ is an odd number, those wherein $n$ is an odd number and $R_1$ is hydrogen and particularly 2-methyl-5-thiazole propanol and 2-propyl-5-thiazole pentanol.

The compositions may be in the form of tablets, dragees, gelules, granules, suppositories, and injectable solutions or suspensions prepared in the usual manner.

The compositions may contain the usual excipients such as talc, gum arabic, lactose, starch, magnesium stearate, cacao butter, aqueous or non-aqueous vehicles, fatty bodies of animal or vegetable origin, paraffinic derivatives, glycols, diverse wetting agents, dispersants or emulsifiers or preservatives.

The compositions are useful for the treatment of acute or chronic hyperlipemia, coronary insufficiencies, cardiac insufficiencies of atheromatosis origin and chronic anginia states.

The novel method of the invention for inducing hypolipemic activity in warm-blooded animals, including humans, comprises administering to warm-blooded animals in hypolipemically effective amount of at least one compound of formula I and their non-toxic, pharmaceutically acceptable acid addition salts. The compounds may be administered orally, rectally or parenterally. The usual daily dose is 2 to 50 mg/kg depending upon the compound and the method of administration.

In the following examples there are described several preferred embodiments to illustrate the invention. However, it is to be understood that the invention is not intended to be limited to the specific embodiments.

EXAMPLE 1

2-METHYL-5-THIAZOLE-PROPANOL

STEP A: 3-(2-methyl-5-thiazolyl)-2-propenoic acid

A mixture of 29 g of 2-methyl-5-thiazolecarboxaldehyde, 30 ml of pyridine, 29 g of malonic acid and 30 drops of piperidine was heated at 100°–110° C for 5 hours and after cooling to room temperature, the mixture was poured into 500 ml of water. The pH of the mixture was adjusted to 3 by addition of N sulfuric acid and the mixture was vacuum filtered. The recovered precipitate was dried to obtain 27.8 g of product which was crystallized from 800 ml of water containing 10% ethanol to obtain 23.8 g of 3-(2-methyl-5-thiazolyl)-2-propenoic acid with a melting point of 204° C.

STEP B: 2-methyl-5-thiazole-propanoic acid

Hydrogen was passed through a mixture of 10 g of 3-(2-methyl-5-thiazolyl)-2-propenoic acid, 260 ml of ethanol, 15 ml of triethylamine and 5 g of activated carbon containing 10% palladium for an hour and the mixture was then filtered and the filter was washed with ethanol. The filtrate was evaporated to dryness and the 13.3 g of colorless oil was dissolved in 100 ml of water. Sulfur dioxide was bubbled through the solution until the pH was acid and excess sulfur dioxide was removed with nitrogen bubbling. The mixture was vacuum filtered and the recovered precipitate was washed and dried to obtain 7.1 g of crystalline product which was crystallized to obtain 6.5 g of 2-methyl-5-thiazole-propanoic acid melting at 120° C.

STEP C: methyl 2-methyl-5-thiazole-propanoate

A mixture of 31.7 g of 2-methyl-5-thiazole-propanoic acid, 3.2 ml of concentrated sulfuric acid and 300 ml of methanol was refluxed for 16 hours and was concentrated under reduced pressure. The mixture was added to 100 ml of water and concentrated ammonium hydroxide was added to obtain a pH of 12–13. The mixture was extracted with methylene chloride and the organic extracts were dried over magnesium sulfate and concentrated to dryness under reduced pressure to obtain 35 g of raw methyl 2-methyl-5-thiazole-propanoate. The hydrochloride thereof melted at 115° C.

STEP D: 2-methyl-5-thiazole-propanol 10.9 g of methyl 2-methyl-5-thiazole-propanoate in 70 ml of tetrahydrofuran was slowly added with stirring at 10°–15° C to a mixture of 125 ml of tetrahydrofuran and 3.42 g of lithium aluminum hydride at 10° C and the mixture was stirred for about 30 minutes. Then, tetrahydrofuran containing 20% water was slowly added and the mixture was filtered. The filter was washed with ethyl acetate and the filtrate was dried over magnesium sulfate and concentrated under reduced pressure to obtain 8.4 g of raw product which was rectified under reduced pressure to obtain 6.4g of 2-methyl-5-thiazole propanol with a boiling point of 106° C under 0.05 mm Hg.

Analysis: $C_7H_{11}NOS$; Calculated: %C, 53.47; %H, 7.05; %N, 8.90; %S, 20.39. Found: %C, 53.2; %H, 7.2; %N, 8.6; %S, 20.1.

EXAMPLE 2

2-propyl-5-thiazole-pentanol

STEP A: 2-propyl-5-thiazolecarboxaldehyde 100 g of manganese dioxide were added to 21 g of 2-propyl-5-thiazole-methanol in 1000 ml of benzene and the mixture was stirred for 3 hours at room temperature. 40 g of manganese dioxide were added and the mixture was stirred at room temperature for 2 hours after which another 20 g of managanese dioxide was added. The mixture was stirred for 16 hours at room temperature and was filtered and the filter was washed with methylene chloride. The filtrate was evaporated to dryness under reduced pressure to obtain 18.5 g of 2-propyl-5-thiazolecarboxaldehyde.

STEP B: ethyl 5-(2-propyl-5-thiazolyl)-2,4-pentadienoate 28.5 g of triethylphosphonate in 40 ml of tetrahydrofuran were added to a stirred mixture of 5.5 g of sodium hydride as a 50% dispersion in oil and 100 ml of tetrahydrofuran cooled to 0° C and then a mixture of 17.5 g of 2-propyl-5-thiazolecarboxaldehyde in 40 ml of tetrahydrofuran was added. Stirring at 0° C was continued for 15 minutes and the mixture was poured into 300 ml of ice water. The mixture was extracted with methylene chloride and the organic extracts were washed with water, dried over magnesium sulfate and concentrated to dryness under reduced pressure to obtain 35 g of raw product. The latter was chromatographed over silica gel and eluted with ethyl acetate to obtain 16 g of ethyl 5-(2-propyl-5-thiazolyl)-2,4-pentadienoate melting at 52° C.

STEP C: ethyl 2-propyl-5-thiazole-pentanoate

Hydrogen was passed through a mixture of 25 g of ethyl 5-(n-propyl-5-thiazolyl)-2,4-pentadienoate, 250 ml of ethanol and 12.5 g of activated carbon containing 10% palladium with stirring for 2 hours and the mixture was filtered and the filter was washed with ethanol. The filtrate was evaporated to dryness under reduced pressure to obtain 23 g of raw ethyl 2-propyl-5-thiazole-pentanoate.

STEP D: 2-propyl-5-thiazole-pentanol

A mixture of 23 g of ethyl 2-propyl-5-thiazole-pentanoate in 150 ml of anhydrous tetrahydrofuran was added to a stirred mixture of 250 ml of tetrahydrofuran and 5 g of lithium aluminum hydride maintained at 0° C and the mixture was stirred for 30 minutes. Excess hydride was destroyed by slow addition of tetrahydrofuran containing 10% water while keeping the temperature at 15°–20° C and then an aqueous solution saturated with sodium potassium tartrate was slowly added thereto. The mixture was filtered and the filter was washed with ethyl acetate. The filtrate was dried over magnesium sulfate and was evaporated under reduced pressure to obtain 20 g of a pale yellow oil which was rectified to obtain 15 g of 2-propyl-5-thiazole-pentanol in the form of a colorless oil with a boiling point of 122° C at 0.1 mm Hg.

Analysis: $C_{11}H_{19}NOS$; Calculated: %C, 61.93; %H, 8.98; %N, 6.56; %S, 15.03. Found: %C, 61.7; %H, 9.2; %N, 6.3; %S, 14.9.

Using the same procedure, ethyl 2-methyl-5-thiazoleacetate was reduced to obtain 2-methyl-5-thiazole-ethanol. Also, ethyl 2-propyl-5-thiazole acetate was reduced to obtain 2-propyl-5-thiazole-ethanol.

EXAMPLE 3

Tablets were prepared containing 300 mg of 2-methyl-5-thiazole-propanol and sufficient excipient consisting of lactose, wheat starch, treated starch, rice starch, talc and magnesium stearate. Gelules were prepared containing 300 mg of 2-propyl-5-thiazole-pentanol and sufficient excipient of talc, aerosil 0 and magnesium stearate to obtain a final weight of 350 mg.

PHARMACOLOGICAL DATA

A. Acute toxicity

Acute toxicity was determined on groups of 10 mice weighing between 18 to 22 g and the product of Example 1 was administered intraperitoneally as a suspension in carboxymethyl cellulose. The animals were observed for 1 week and the average lethal dose $DL_{50}$ was found to be greater than 1000 mg/kg.

B. Antilipolytic Activity

Male rats of the Sprague Dawley SPF strain weighing about 180 to 200 g were starved for 24 hours and then were given the compound of Example 1 orally. One hour after the oral administration, the animals were killed by carotidienne section and samples of blood were obtained to determine the level of free fatty acids. The extraction of free fatty acids was made by the technique of Dole [J. Clin. Invest., Vol. 38 (1959), p. 1544–15544] as modified by Trout et al [J. Lipid Res., Vol. 1 (1960), p. 199–202]. The plasmatic extract free of phospholipids was colorimetrically determined by the method of Anthonis [J. Lipid. Res., Vol. 6 (1965), p. 307–312]. Under these test conditions, the dose of the product of Example 1 which reduced by 50% the level of free fatty acids in the treated animals as compared to the controls ($DA_{50}$) was found to be ≃ 2mg/kg. This shows that the product clearly reduces the level of free plasmatic fatty acids.

Various modifications of the products and methods of the invention may be made without departing from the spirit or scope thereof and it should be understood that the invention is to be limited only as defined in the appended claims.

We claim:

1. A hypolipemiant composition comprising an hypolipemiantly effective amount of at least one compound selected from the group consisting of a thiazole of the formula

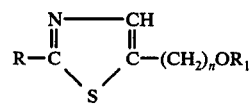

wherein R is alkyl of 1 to 5 carbon atoms, $n$ is an integer of 3,5 or 7 and $R_1$ is selected from the group consisting of hydrogen and acyl of an alkanoic acid of 2 to 6 carbon atoms and their non-toxic, pharmaceutically acceptable acid addition salts and a pharmaceutical carrier.

2. A composition of claim 1 wherein $R_1$ is hydrogen.

3. A method of inducing hypolipemic activity in warm-blooded animals comprising administering to warm-blooded animals an hypolipemically effective amount of at least one compound selected from the group consisting of the formula

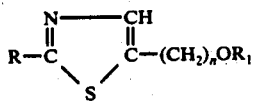

wherein R is alkyl of 1 to 5 carbon atoms, $n$ is an integer of 3,5 or 7 $R_1$ is selected from the group consisting of hydrogen and acyl of an alkanoic acid of 2 to 6 carbon atoms and their non-toxic, pharmaceutically acceptable acid addition salts.

4. The method of claim 3 wherein $R_1$ is hydrogen.

5. The method of claim 3 wherein the compound is 2-methyl-5-thiazole-propanol.

6. The method of claim 3 wherein the compound is 2-propyl-5-thiazole-pentanol.

* * * * *